US 9,115,111 B2

(12) United States Patent
Cramail et al.

(10) Patent No.: US 9,115,111 B2
(45) Date of Patent: Aug. 25, 2015

(54) BICARBONATE PRECURSORS, METHOD FOR PREPARING SAME AND USES THEREOF

(75) Inventors: Henri Cramail, Sainte Terre (FR); Aurelie Boyer, Bordeaux (FR); Eric Cloutet, Saint Caprais de Bordeaux (FR); Benoit Gadenne, Villenave d'ornon (FR); Alfos Carine, Pessac (FR)

(73) Assignee: CENTRE NATIONAL DE LA RECHERCHE SCIENTIFIQUE (C.N.R.S.), Paris (FR)

( * ) Notice: Subject to any disclaimer, the term of this patent is extended or adjusted under 35 U.S.C. 154(b) by 310 days.

(21) Appl. No.: 13/510,625

(22) PCT Filed: Nov. 19, 2010

(86) PCT No.: PCT/FR2010/052457
§ 371 (c)(1),
(2), (4) Date: Jun. 27, 2012

(87) PCT Pub. No.: WO2011/061452
PCT Pub. Date: May 26, 2011

(65) Prior Publication Data
US 2012/0259087 A1    Oct. 11, 2012

(30) Foreign Application Priority Data

Nov. 20, 2009   (FR) .................................... 09 58219

(51) Int. Cl.
| C08F 2/48 | (2006.01) |
| C07D 317/36 | (2006.01) |
| C08G 64/30 | (2006.01) |
| C07D 317/38 | (2006.01) |
| C08G 71/04 | (2006.01) |

(52) U.S. Cl.
CPC ............ *C07D 317/36* (2013.01); *C07D 317/38* (2013.01); *C08G 64/30* (2013.01); *C08G 71/04* (2013.01)

(58) Field of Classification Search
CPC ..... C08G 64/30; C07D 317/36; C07D 317/38
USPC .......................................... 528/370; 568/624
See application file for complete search history.

(56) References Cited

U.S. PATENT DOCUMENTS

| 4,542,173 A | 9/1985 | Schupp et al. |
| 4,808,658 A | 2/1989 | Walz et al. |
| 2008/0286486 A1* | 11/2008 | Herlihy et al. ................. 427/521 |

FOREIGN PATENT DOCUMENTS

| EP | 0001088 A1 | 3/1979 |
| EP | 0212409 A2 | 3/1987 |
| EP | 0229622 A2 | 7/1987 |
| EP | 0661354 A1 | 7/1995 |
| WO | 2007055929 A1 | 5/2007 |

OTHER PUBLICATIONS

Bobyleva et al., "Condensation of Olefin Oxides with Carbon Dioxide in the Presence of Metal Chloride-dimethylformamide Catalyst", Neftehimia/Neftechimija, Akademia Nauk SSSR, vol. 36. No. 3, Jan. 1, 1996, pp. 209-213, XP009132962.
Burgel et al., "Reaction of Cyclic Carbonates with Amines: Linear Telechelic Oligomers", Polymer Bulletin, vol. 30, No. 2, 1993, pp. 155-162, XP002599513.
Kihara et al. "Synthesis and Properties of Poly(hydroxyurethanes)", Journal of Polymer Science, Part A: Polymer Chemistry, vol. 31, No. 11, 1993, pp. 2765-2773, XP002599514.
Ondruschka et al., "Incorporation of C02 into Various Terminal and Internal Epoxides", Collection of Czechoslovak Chemical Communications, Institute of Organic Chemistry & Biochemistry, vol. 73, No. 1, Jan. 1, 2008, pp. 88-96, XP002581705.
Rokicki et al., "Studies on the Synthesis of Poly(hydroxyurethanes)s from Diepoxides Carbon Dioxide and Diamines", Polimery, Instytut Chemii Przemysowej, vol. 34. No. 4, Jan. 1, 1989, pp. 140/141-147. XP009132957.
Webster et al., "Cyclic Carbonate Functional Polymers: Synthesis and Applications", Polymer News, vol. 23, No. 6, Jan. 1, 1998, pp. 187-192, XP009078653.
International Search Report dated May 26, 2011, from corresponding PCT application.

* cited by examiner

*Primary Examiner* — Gregory Listvoyb
(74) *Attorney, Agent, or Firm* — Young & Thompson

(57) ABSTRACT

The present invention concerns a compound of following formula (I):

where:
$R_1$ is H or an alkyl group,
$A_1$ is a divalent straight-chain or branched alkylene radical, and
$A_2$ is a —O-$A_4$-O— radical, $A_4$ is a divalent straight-chain or branched alkylene radical.

22 Claims, No Drawings

BICARBONATE PRECURSORS, METHOD FOR PREPARING SAME AND USES THEREOF

The subject of the present invention concerns bicarbonate precursors and their method of preparation. A further subject is the use thereof for the preparation of polyurethanes.

The synthesis of linear polyurethanes entails the reaction between a diol and a diisocyanate. Isocyanates are toxic compounds which are obtained from phosgene, itself highly toxic when inhaled, causing buns. The industrial process used is the reaction of an amine with excess phosgene to form an isocyanate and a mixture of hydrogen chloride and phosgene.

The search for alternatives to the synthesis of polyurethanes without isocyanates is therefore a major challenge.

At the present time, the carbonatation of triglycerides is known. However, the carbonatation of triglycerides leads to obtaining synthons having an ill-defined number of cyclic carbonate groups. The functionality of these precursors is therefore not controlled and is higher than 2.

The objective of the present invention is to provide synthons having controlled functionality.

The objective of the present invention is to provide synthons having a functionality of exactly 2.

A further objective of the present invention is the synthesis of linear polymers having controlled structures and properties from synthons having a controlled functionality of exactly 2.

The present invention therefore concerns the compounds of following formula (I):

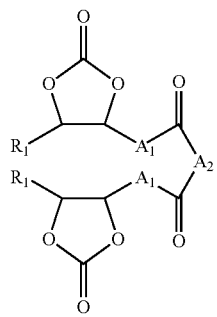

(I)

where:
- $R_1$ is H or a straight-chain or branched alkyl group comprising 1 to 20 carbon atoms,
- $A_1$ is a divalent, straight-chain or branched alkylene radical comprising 2 to 14 carbon atoms, and
- $A_2$ is a —O-$A_4$-O— radical $A_4$ being a divalent straight-chain or branched alkylene radical comprising 1 to 20 carbon atoms, preferably 1 to 10 carbon atoms, optionally comprising one or more substituents or being interrupted by one or more groups chosen in particular from the group formed by the phenylene radical and the radical of formula —$(CH_2OCH_2)_n$—, n representing an integer of between 1 and 100, preferably 6 to 50, and is preferably 6, 13 or 45, or $A_2$ is a radical of formula —$(OCH_2CH_2)_n$—O—, n being such as defined above.

For example the above-mentioned radical $A_4$ may be a radical having the formula —$CH_2$-$A_3$-$CH_2$—, $A_3$ being a group of formula —$(CH_2OCH_2)_n$—, n representing an integer of between 1 and 100, preferably it is 6, 13 or 45, or a phenylene radical.

According to one preferred embodiment, the compounds of the present invention meet the following formula (I-1):

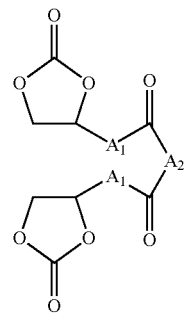

(I-1)

$A_1$ and $A_2$ being such as defined above in formula (I).

These compounds are therefore compounds of formula (I) such as defined above where $R_1$ is H.

Another family of preferred compounds of the invention is formed of compounds of formula (I) such as defined above where $R_1$ is a straight-chain or branched alkyl group, comprising 1 to 20 carbon atoms and preferably 1 to 12 carbon atoms.

According to one particular embodiment, in the above-mentioned formula (I) $A_1$ is a straight-chain alkylene radical comprising 7 carbon atoms.

According to another particular embodiment, in the above-mentioned formula (I), $A_4$ is a straight-chain alkylene radical comprising 3, 4, 5 or 6 carbon atoms.

Another family of preferred compounds according to the invention is formed by the compounds of formula (I-2) such as defined below,

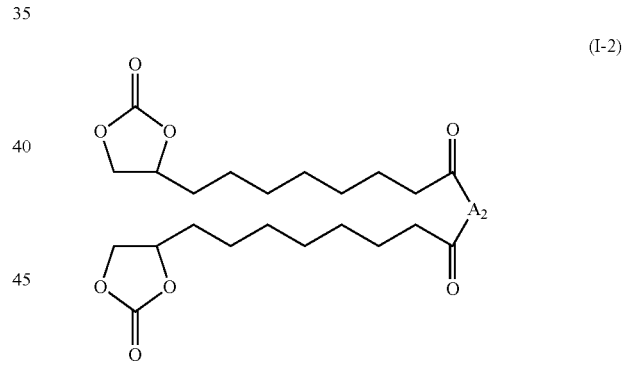

(I-2)

$A_2$ being such as defined above.

Another family of preferred compounds of the invention is formed by compounds of formula (I-3) such as defined below,

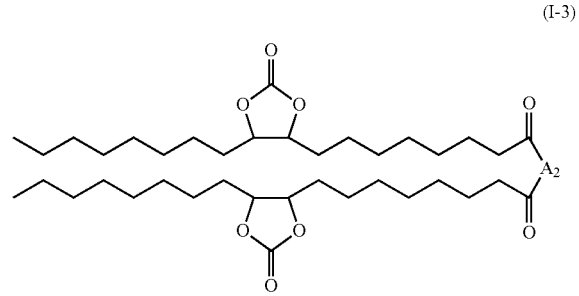

(I-3)

$A_2$ being such as defined above.

The present invention also concerns a method for preparing a compound of formula (I) such as defined above, comprising a carbonatation step of a compound of following formula (II):

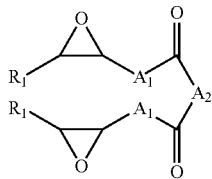

(II)

$A_1$, $A_2$ and $R_1$ being such as defined in formula (I), and $R_1$ preferably being H.

Preferably, this carbonatation step is conducted in the presence of $CO_2$ in any form, for example in liquid, gaseous or supercritical form (depending on pressure), and of a reagent chosen from among tetrabutylammonium bromide, tetrabutylammonium hydroxide and the mixtures of tin tetrachlorides ($SnCl_4:5H_2O$). It is preferably conducted in the presence of supercritical $CO_2$ and tetrabutylammonium bromide.

According to one advantageous embodiment, the above-mentioned carbonatation step is conducted at a temperature of between 80° C. to 150° C., and preferably at 120° C. If the temperature is lower than 80° C., the kinetics are far too slow and the activation energy is insufficient, and if the temperature is higher than 150° C. degradation of the catalyst is observed.

Preferably, at the above-mentioned carbonatation step, the carbon dioxide is added at a pressure of between 100 bar to 200 bar.

According to one particularly advantageous embodiment, the compound of formula (II) such as defined above is prepared by epoxidation of the compound of following formula (III):

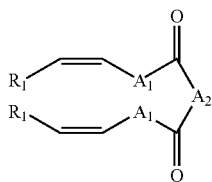

(III)

$A_1$, $A_2$ and $R_1$ being such as defined in formula (I).

According to one preferred embodiment, step b) of the method of the invention is conducted in the presence of a peracid, this step in particular being performed under a vacuum at 200° C. for at least 3 minutes.

Among the peracids, particular mention may be made of metachloroperbenzoic acid (m-CPBA) and magnesium monoperoxyphthalate hexahydrate peracid (MMPP).

The specificity of this method lies in the use of a preformed peracid.

According to one particularly advantageous embodiment, the compound of formula (III) such as defined above is prepared by transesterification of a compound of following formula (IV):

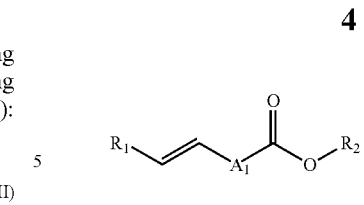

(IV)

with a diol of following formula (V):

(V)

$R_1$, $A_1$ and $A_2$ being such as defined in formula (I), and
$R_2$ being a straight-chain or branched alkyl group comprising 1 to 10, preferably 1 to 6 carbon atoms.

The method of the invention for preparing compounds (III) consists of a transesterification step conducted under heterogeneous catalysis (magnesium oxide or other heterogeneous catalyst) and preferably in the absence of a solvent (clean synthesis).

According to one preferred embodiment, this transesterification step is conducted in the presence of a catalyst chosen from the group formed by magnesium oxide, zinc acetate and sodium methanolate.

Preferably this step is conducted at a temperature of between 150 to 200° C. under a flow of nitrogen. This temperature range is chosen in relation to the type of catalyst used. For example, if the temperature is higher than 200° C., the catalyst is degraded.

According to one preferred embodiment, this step is conducted solvent-free which is highly advantageous in ecological terms.

The present invention therefore concerns a method for preparing a compound of formula (I) such as defined above, comprising the following steps:

a) a transesterification step of a compound of following formula (IV):

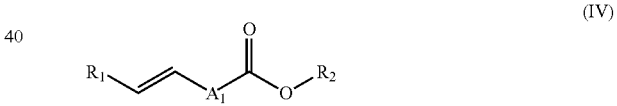

(IV)

with a diol of following formula (V):

(V)

$R_1$, $A_1$ and $A_2$ being such as defined in formula (I), and
$R_2$ being a straight-chain or branched alkyl group comprising 1 to 10, preferably 1 to 6 carbon atoms, to obtain a compound of following formula (III):

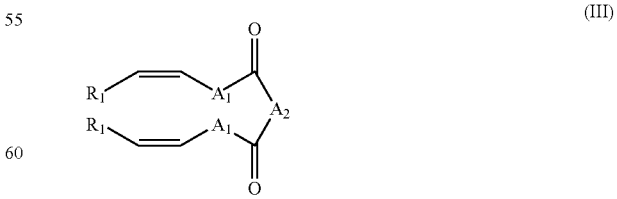

(III)

$R_1$, $A_1$ and $A_2$ being such as defined in formula (I), b) an epoxidation step of the compound of above-mentioned formula (III) to obtain a compound of following formula (II):

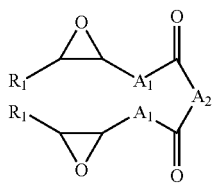

(II)

$R_1$, $A_1$ and $A_2$ being such as defined in formula (I), c) a carbonatation step of the compound of above-mentioned formula (II) to obtain a compound of formula (I) such as defined above, and d) a step to recover the compound of formula (I) such as defined above.

The above-mentioned method of the invention may also comprise an intermediate step between step a) and step b) which consists of purifying the compounds of formula (III), in particular on a silica column or by distillation under a high vacuum.

The above-mentioned method of the invention may also comprise an intermediate step between step b) and step c) which consists of purifying the compounds of formula (II), in particular on a silica column.

DETAILED DESCRIPTION OF THE STEPS OF THE METHOD OF THE INVENTION

1. Transesterification Reaction of the Compounds of Formula (IV)

For the method of the invention, this transesterification is preferably conducted starting from an ester of a light alcohol (in particular methanol or ethanol . . . ) of oleic sunflower (formula (IV) compound)) and a diol (formula (V) compound) in the particular presence of magnesium oxide as catalyst. Several syntheses are conducted with different diols to modulate the properties of the monomers and hence of the resulting polymers. Transesterifications were therefore performed from propanediol, butanediol, pentanediol, hexanediol, ethylene polyoxide and 1,4-benzenedimethanol.

The reaction takes place at 150° C. and 200° C. under a flow of nitrogen. The progress of the reaction is monitored by different analyses and in particular by NMR (disappearance of the methyl group singlet).

Less diol is added (for example 0.5 mol per 1 mol of formula (IV) compound).

The synthesis route used is <<clean>> since it has recourse to heterogeneous catalysis (magnesium oxide) and the synthesis takes place solvent-free. Industrial purification can use distillation under a high vacuum.

2. Epoxidation of the Compounds Obtained After Transesterification

The epoxidation of fats having a primary alcohol at the end of the chain using peracids formed in situ has never been described and cannot be conducted under the same conditions as those described previously. The epoxidation reaction is effectively interfered by a secondary oxidation reaction of the terminal alcohol of the oleic sunflower monoester to form a carboxylic acid. Since the reagent is consumed by this secondary reaction, epoxidation does not occur.

The process used in the method of the invention for epoxidation of the compounds of formula (III) lies in the use of a peracid that is already prepared and commercially available, namely metachloroperbenzoic acid (m-CPBA), and therefore avoids the use of potentially toxic metals.

In the invention, epoxidation is performed with peracids (mCPBA, MMPP . . . ). The reaction can be monitored by NMR; the disappearance of the doublets of the protons of the double bond at 5.2 ppm and the onset of a wide peak at 2.8 ppm allow the progress of the reaction to be monitored. Total conversion of the double bonds is obtained after 3 h. The excess m-CPBA is reduced to corresponding carboxylic acid with a saturated solution of sodium sulfate. The organic phase is extracted with dichloromethane then the residual carboxylic acid is converted to sodium chlorobenzoate (soluble in water) by means of two washings with a saturated sodium bicarbonate solution.

The present invention also concerns the use of the compounds of formula (I) such as defined above, for the preparation of polyurethane.

The synthesis of polyurethanes from epoxidated vegetable oils and carbon dioxide overcomes the need to use isocyanates which are toxic compounds. The reaction involved is the obtaining of a cyclic carbonate group through the reaction of the epoxide group of the vegetable oil with $CO_2$. During polymerization, the carbonate then reacts with a hydrogen donor e.g. an amine to form a urethane function.

The present invention also concerns the polyurethanes such as obtained by reaction of the formula (I) compounds with a hydrogen donor.

The present invention also concerns the use of the compound of formula (II) such as defined above in which $R_1$ is H, for the preparation of polyepoxide resins.

The present invention also concerns the polyepoxide resins as obtained by reaction of the compounds of formula (II) such as defined above in which $R_1$ is H, with a hydrogen donor.

Experimental Part

Example 1

Preparation of Bicarbonates with Internal Cyclic carbonate Groups

These compounds are prepared in accordance with the following reaction scheme:

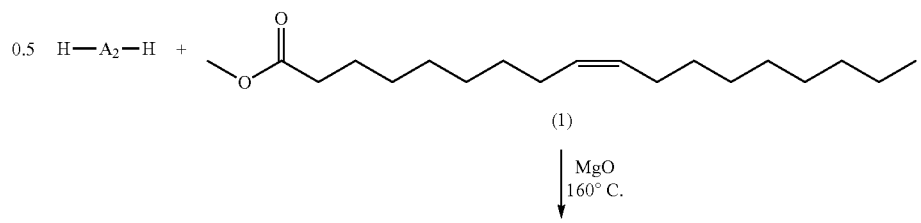

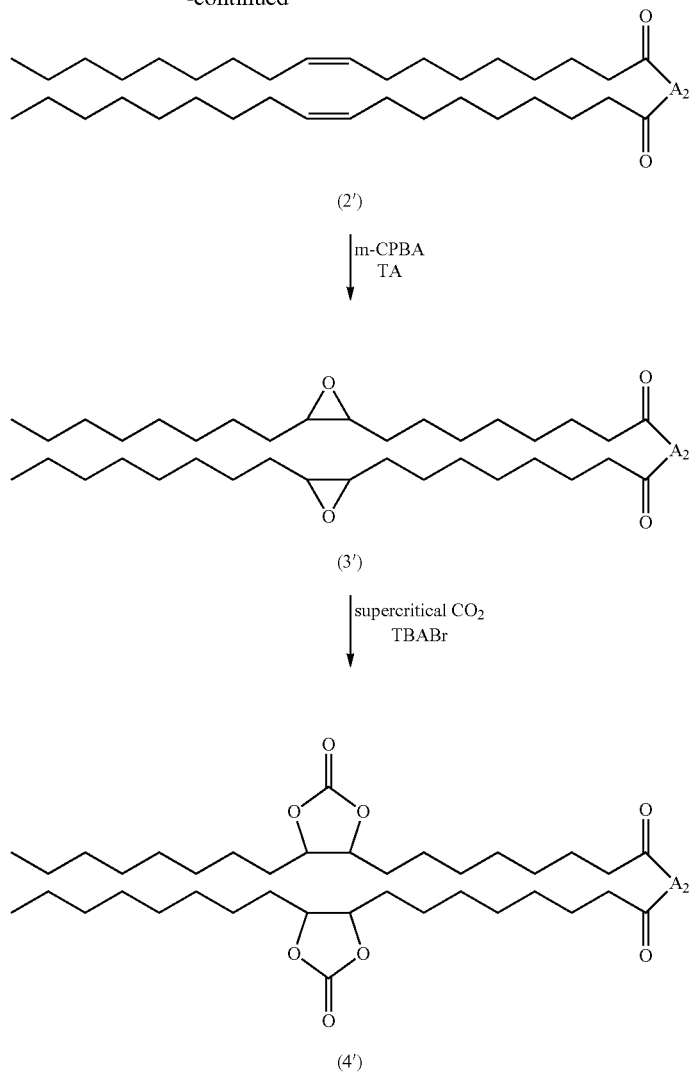

Compound 4' corresponds to a compound of formula (I-3) such as defined above. In this compound, $A_2$ may be a radical chosen from among the following radicals: $—OC_3H_6O—$, $—OC_4H_8O—$, $—OC_5H_{10}O—$, $—OC_6H_{12}O—$, $—OH_2C—(CH_2OCH_2)_6—CH_2O—$, $—OH_2C—(CH_2OCH_2)_{13}—CH_2O—$, $—OH_2C—(CH_2OCH_2)_{45}—CH_2O—$ or $—OH_2C—C_6H_4—CH_2O—$.

Step 1: Synthesis of Compound 2'

A transesterification reaction is carried out of oleic methyl ester (1) with a diol H-$A_2$-H ($A_2$ being such as defined above).

The oleic methyl ester (1) is placed in a 250 mL flask equipped with a Dean Stark trap and surmounted by a cooler. The reaction takes place in a vacuum in the presence of 0.5 diol equivalent to promote the formation of diesters (2'); it is catalysed with 1 wt % magnesium oxide. The temperature of the medium is raised to 160° C., and the methanol produced is continuously removed by means of the Dean Stark trap. After 7 h, the temperature is raised to 180° C. for 30 minutes to remove residual oleic methyl ester (1). Yield: 95%.

The above-described protocols are the same independently of the type of diols used for transesterification (i.e. independently of the nature of $A_2$). The different diols used are: propanediol, butanediol, pentanediol, hexanediol, ethylene polyoxide (300 g/mol, 600 g/mol and 2 000 g/mol) and 1,4-benzenedimethanol.

It is to be noted that transesterification with 1,4-benzenedimethanol is conducted at 140° C. to avoid sublimation of the diol.

Step 2: Synthesis of Compound 3'

The transesterified oleic methyl ester (2') is placed in 100 mL of metachloroperbenzoic acid (m-CPBA) (1.2 eq per double bond). The mixture is left under agitation at ambient temperature. Total conversion of the double bonds is obtained after 3 h. The excess m-CPBA is reduced to corresponding carboxylic acid with a saturated solution of sodium sulfate (100 mL). The organic phase is extracted with dichloromethane then the residual carboxylic acid is converted to sodium chlorobenzoate (soluble in water) by two washings with a saturated solution of sodium bicarbonate (2×100 mL). Yield: 80%.

Step: Synthesis of Compound 4'

Carbonatation takes place in the presence of compound (3') and 1 wt % tetrabutylammonium bromide (TBABr), in a high pressure reactor; the reactor is heated to a temperature of 120° C. then carbon dioxide is added until a pressure of 100 bar is reached. The reaction is halted when there is total conversion of the epoxides. Yield: 90%.

Example 2
Preparation of Bicarbonates with Terminal Cyclic Carbonate Groups
These compounds are prepared as per the following reaction scheme:
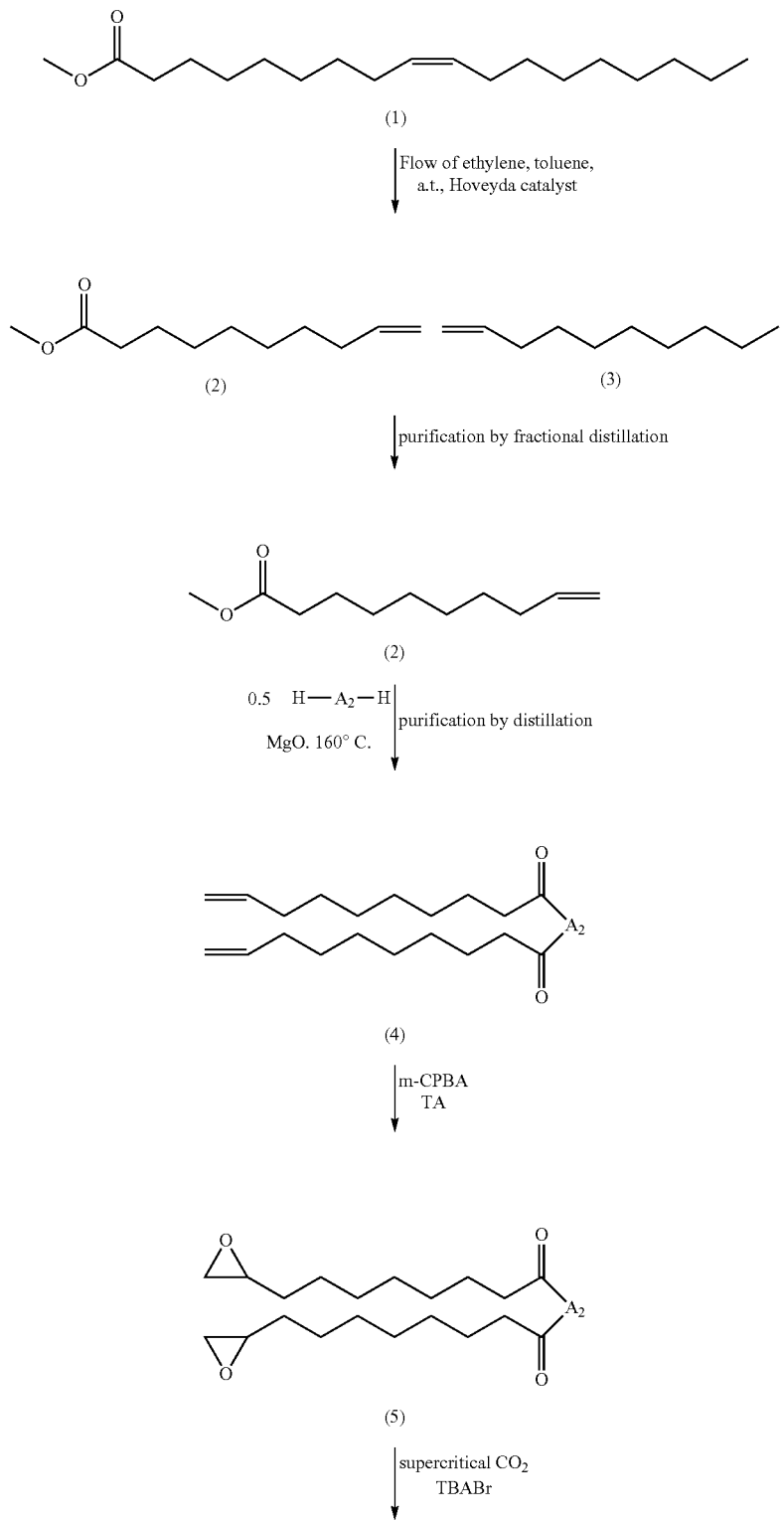

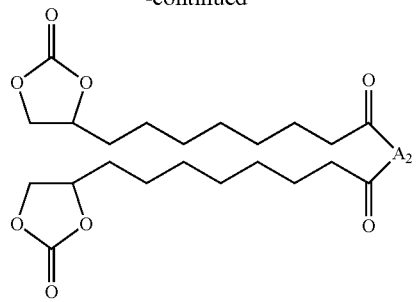

(6)

Compound 6 corresponds to a compound of formula (I-2) such as defined above. In this compound, $A_2$ may be a radical chosen from among the following radicals: $-OC_3H_6O-$, $-OC_4H_8O-$, $-OC_5H_{10}O-$, $-OC_6H_{12}O-$, $-OH_2C-(CH_2OCH_2)_6-CH_2O-$, $-OH_2C-(CH_2OCH_2)_{13}-CH_2O-$, $-OH_2C-(CH_2OCH_2)_{45}-CH_2O-$ or $-OH_2C-C_6H_4-CH_2O-$.

Step 1: Synthesis of Compounds 2 and 3

10 g of dry oleic methyl ester ($3.4.10^{-2}$ mol) (1) are dissolved in 20 mL of distilled toluene, in a 250 mL flask. 250 mg (2.5 wt %) of Hoveyda catalyst are added and 1 bar of ethylene. The medium is left under magnetic agitation at ambient temperature. The reaction is halted after 6 h.

Step 2: Extraction of Compound 2

In equilibrium state, the medium is composed of 48% of starting oleic methyl ester (1), 26% of decene (3) and 26% of methyl-10-undecenoate (2). The latter is extracted by vacuum distillation: the first fraction at 100° C. contains decene (3); the methyl-10-undecenoate (2) is recovered when the temperature reaches 180° C. The residue is composed of oleic methyl ester (1). Total yield of steps 1+2: 25%.

Step 3: Synthesis of Compound 4

A transesterification reaction of methyl-10-undecenoate (2) is carried out using H-$A_2$-H ($A_2$ being such as defined above).

2 g of methyl-l0-undecenoate (1) are placed in a 50 mL flask equipped with a Dean Stark trap and surmounted by a cooler. The reaction takes place in a vacuum in the presence of 0.5 diol equivalent to promote the formation of diesters; it is catalysed with 1 wt % magnesium oxide. The temperature of the medium is raised to 160° C., the methanol produced is continuously removed by means of the Dean Stark trap. After 7 h, the temperature is brought to 180° C. for 30 minutes to remove residual methyl-10-undecenoate. Yield of step 3: 90%

The protocols described above are the same, independently of the type of diols used for transesterification (i.e. independently of the nature of $A_2$). The different diols used are: propanediol, butanediol, pentanediol, hexanediol, ethylene polyoxide (300 g/mol, 600 g/mol and 2 000 g/mol) and 1,4-benzenedimethanol.

It is to be noted that transesterification with 1,4-benzenedimethanol is performed at 140° C. to avoid sublimation of the diol.

Step 4: Synthesis of Compound 5

The last step consists of the epoxidation of the double bonds of the product obtained by transesterification. The transesterified methyl-l0-undecenoate (4) is dissolved in 20 mL of dichloromethane, in a 50 mL flask. Metachloroperbenzoic acid (m-CPBA) is added (1.2 eq per double bond). The mixture is placed under agitation at ambient temperature. Total conversion of the double bonds is obtained after 3 h. The excess m-CPBA is reduced to corresponding carboxylic acid with a saturated solution of sodium sulfate (30 mL). The organic phase is extracted with dichloromethane then the residual carboxylic acid is converted to sodium chlorobenzoate (soluble in water) by two washings with a saturated solution of sodium bicarbonate (2×40 mL). Yield of step 4: 85%

Polycondensation between the bis-epoxide synthon and various diamines leads to the polyepoxide materials.

Step 5: Synthesis of Compound 6

Carbonatation takes placed in the presence of compound (5) and 1 wt % of tetrabutylammonium bromide (TBABr), in a high pressure reactor. The temperature of the reactor is brought to 120° C. then carbon dioxide is added until a pressure of 100 bar is reached. The reaction is halted when there is full conversion of the epoxides. Yield: 90%

Example 3

Synthesis of Polymers from Different Bicarbonate Precursors (Terminal and Internal)

1 g of bicarbonate precursor (4') or (6) is added to a diamine (e.g.: ethylenediamine (EDA), isophorone diamine (IPDA), hexamethylenediamine (NMDA), aminoethyl-piperazine (AEP), diethylenetriamine), in a 50 mL flask. The number of amine groups is added in stoichiometric proportion relative to the number of carbonate functions of compound (4') or (6). The mixture is left under magnetic agitation, at 70° C. The disappearance of the carbonate group is monitored by infrared analysis (disappearance of the band at 1 803 $cm^{-1}$). The reaction is halted after 8 h. The molar weight of the polymer is obtained by size exclusion chromatography and its glass transition temperature is measured by Differential Scanning Calorimetry.

Example with $A_2 = -OC_5H_{10}O-$:

1 g of (4') is added to a 50 mL flask in the presence of 0.079 g EDA. The mixture is left under magnetic agitation at 70° C. The reaction is halted after 8 h. The molar weight of the polymer is obtained by size exclusion chromatography and its glass transition temperature is measured by Differential Scanning Calorimetry.

The same protocol is applied for $A_4$=PEG300 and $-CH_2-C_6H_4-CH_2-$ (cf. formula (I)).

The table below gives the results (glass transition temperature and molar weight):

| Polymers from bicarbonates (4') and EDA | $T_g$ (° C.) | $M_w$ (g/mol) |
|---|---|---|
| $A_4$ = PEG$_{300}$ | −55 | 12 200 |
| $A_4$ = C$_5$H$_{10}$ | −20 | 14 500 |
| $A_4$ = 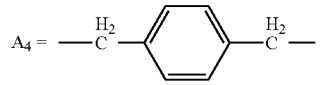 | −15 | 13 400 |

Example 4

Synthesis of Polyepoxide Resins from Bis-Epoxide Precursors (Compounds of Formula (II) where $R_1$=H)

Polycondensation between the bis-epoxide synthon and various diamines leads to the polyepoxide materials.

Example of Polyepoxide Resins:

0.5 g of compound (5) (1.06e$^{-3}$ mol) are placed in an aluminium dish with diethylenetriamine (or ethylenediamine (EDA), hexamethyldiamine (HMDA), isophoronediamine (IPDA) and aminoethyl piperazine AEP). The number of amine groups is added in stoichiometric proportion relative to the number of epoxide functions of compound (5). The mixture is then placed in a rectangular mould (length 1 cm, thickness and width 0.5 cm) and placed in an oven at 90° C. for 24 h. The glass transition temperature of the synthesized resins is determined by Differential Scanning Calorimetry.

The table below gives the results obtained (glass transition temperatures of the epoxy resins derived from polycondensation between compound (5) and different di- or triamines):

| Epoxy resins from bis-epoxides | EDA | HMDA | DETA | IPDA | AEP |
|---|---|---|---|---|---|
| $A_4$ = PEG$_{300}$ | −60° C. | −52° C. | −50° C. | −47° C. | −46° C. |
| $A_4$ = C$_5$H$_{10}$ | −17° C. | −17° C. | | | |
| $A_4$ = —CH$_2$—C$_6$H$_4$—CH$_2$— | −9° C. | 2° C. | 0° C. | 5° C. | |

Example of Epoxy Resins Formed from a Mixture of Bisphenol A Diglycidyl Ether (BADGE) and Compound (5). where $A_2$=-OC$_{5H10}$O—

0.48 g of BADGE (M$_{BADGE}$=340.4 g/mol) are mixed in an aluminium dish with 0.12 g of compound (5) (R=C$_5$H$_{10}$). 0.068 g of DETA are added. The mixture is then placed in a rectangular mould (length 1 cm, thickness and width 0.5 cm) and placed in an oven at 90° C. for 24 h.

The same protocol is applied changing the proportions of BADGE.

The glass transition temperatures of the synthesized resins are determined by Differential Scanning Calorimetry.

The results obtained are given below:

| Proportion of BADGE | $T_g$ of the epoxy resin (° C.) |
|---|---|
| 100% | 120 |
| 80% | 95 |
| 60% | 70 |
| 40% | 55 |
| 20% | 15 |
| 0% | 0 |

The invention claimed is:

1. A compound of following formula (I):

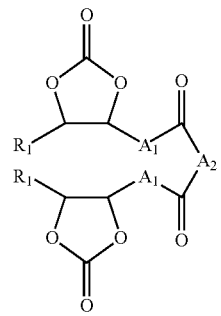

(I)

where:
$R_1$ is H or a straight-chain or branched alkyl group comprising 1 to 20 carbon atoms,
$A_1$ is a divalent straight-chain or branched alkylene radical comprising 2 to 14 carbon atoms, and
$A_2$ is a —O-$A_4$-O— radical, $A_4$ being a divalent straight-chain or branched alkylene radical comprising 1 to 20 carbon atoms, optionally comprising one or more substituents, or being interrupted by one or more groups chosen in particular from the group formed by the phenylene radical and the radical of formula —(CH$_2$OCH$_2$)$_n$—, n representing an integer of between 1 and 100, or $A_2$ is a radical of formula —(OCH$_2$CH$_2$)$_n$—O—, n being as previously defined.

2. The compound according to claim 1, wherein A4 is a divalent straight-chain or branched alkylene radical comprising 1 to 10 carbon atoms.

3. The compound according to claim 1, wherein n is an integer of between 6 and 50.

4. The compound according to claim 3, wherein n is 6, 13 or 45.

5. The compound according to claim 1, wherein $R_1$ is H.

6. The compound according to claim 1, wherein $R_1$ is a straight-chain or branched alkyl group comprising 1 to 20 carbon atoms.

7. The compound according to claim 6, wherein $R_1$ is a straight-chain or branched alkyl group comprising 1 to 12 carbon atoms.

8. A method for preparing a compound of formula (I) according to claim 1 comprising a carbonatation step of a compound of following formula (II):

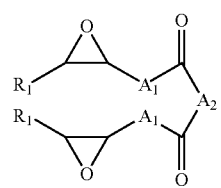

(II)

$A_1$, $A_2$ and $R_1$ being as previously defined.

9. The method for preparing the compound of formula (I) according to claim 8, wherein the carbonatation step is conducted in the presence of supercritical $CO_2$, and tetrabutylammonium bromide.

10. The method according to claim 9, wherein the carbonatation step is conducted at a pressure of between 100 bar to 200 bar.

11. The method according to claim 9, wherein the carbonatation step is conducted at a temperature of between 80° C. to 150° C.

12. The method for preparing the compound of formula (I) according to claim 8, wherein the compound of formula (II) is prepared by epoxidation of the compound of following formula (III):

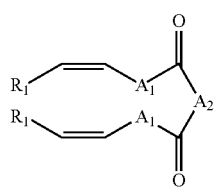
(III)

$A_1$, $A_2$ and $R_1$ being as previously defined, this step preferably being conducted in the presence of a peracid.

13. The method according to claim 12, wherein the peracid is chosen from the group formed by metachloroperbenzoic acid (m-CPBA) and the peracid magnesium monoperoxyphthalate hexahydrate (MMPP).

14. The method according to claim 12, wherein the compound of formula (III) is prepared by transesterification of a compound of following formula (IV):

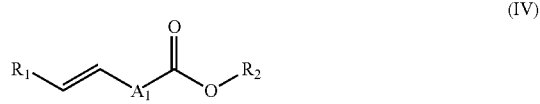
(IV)

with a diol of following formula (V):

(V)

$R_1$, $A_1$ and $A_2$ being such as previously defined, and $R_2$ representing a straight-chain or branched alkyl group comprising 1 to 10 carbon atoms.

15. The method according to claim 14, wherein $R_2$ represents a straight-chain or branched alkyl group comprising 1 to 6 carbon atoms.

16. The method according to claim 15, wherein the transesterification step is conducted in the presence of a catalyst chosen from the group formed by magnesium oxide, zinc acetate and sodium methanolate.

17. The method according to claim 14, wherein the transesterification step is conducted at a temperature of between 150 and 200° C. under a flow of nitrogen.

18. The method according to claim 14, wherein the transesterification step is conducted without solvent.

19. Polymers obtained by reaction of a compound of formula (I) according to claim 11, with hydrogen donor compound.

20. The polymers according to claim 19, wherein the hydrogen donor is chosen from among the amines.

21. The polymers obtained by the reaction of a compound of formula (II) according to claim 8, wherein $R_1$ is H, with a hydrogen donor compound.

22. The polymers according to claim 21, wherein the hydrogen donor is chosen from among the amines.

* * * * *